United States Patent
Lian et al.

(10) Patent No.: US 9,421,378 B2
(45) Date of Patent: Aug. 23, 2016

(54) APPARATUS AND METHOD FOR SPINAL CORD STIMULATION TO TREAT PAIN

(71) Applicant: BIOTRONIK SE & Co. KG, Berlin (DE)

(72) Inventors: Jie Lian, Beaverton, OR (US); Dirk Muessig, West Linn, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 12 days.

(21) Appl. No.: 14/282,115

(22) Filed: May 20, 2014

(65) Prior Publication Data
US 2014/0371811 A1 Dec. 18, 2014

Related U.S. Application Data

(60) Provisional application No. 61/834,887, filed on Jun. 14, 2013.

(51) Int. Cl.
*A61N 1/36* (2006.01)

(52) U.S. Cl.
CPC ....... *A61N 1/36139* (2013.01); *A61N 1/36071* (2013.01); *A61N 1/36135* (2013.01); *A61N 1/36021* (2013.01)

(58) Field of Classification Search
CPC ........... A61N 1/36139; A61N 1/3605; A61N 1/36071
See application file for complete search history.

(56) References Cited

U.S. PATENT DOCUMENTS

| | | | |
|---|---|---|---|
| 6,470,215 B1 | 10/2002 | Kraus et al. | |
| 6,574,509 B1 | 6/2003 | Kraus et al. | |
| 6,622,043 B1 | 9/2003 | Kraus et al. | |
| 2009/0270935 A1 | 10/2009 | Zhao et al. | |
| 2010/0228310 A1* | 9/2010 | Shuros | A61N 1/0551 607/17 |
| 2011/0270329 A1 | 11/2011 | Scheiner | |
| 2013/0030488 A1* | 1/2013 | Cho | A61N 1/3601 607/20 |

FOREIGN PATENT DOCUMENTS

WO 2011093917 8/2011

OTHER PUBLICATIONS

European Search Report and Annex to the European Search Report on European Patent Application No. EP 14 17 1892, dated Sep. 25, 2014 (5 pages).

* cited by examiner

*Primary Examiner* — Eric D. Bertram
(74) *Attorney, Agent, or Firm* — Buchanan Ingersoll & Rooney PC (57) ABSTRACT

A spinal cord stimulation device having a stimulation unit for generation and delivery of stimulation pulses, a control unit for controlling the stimulation unit with respect to stimulation intensity and an autonomic nervous system ("ANS") sensing unit that is configured to generate ANS indicating signals that represent an increased sympathetic tone or an increased parasympathetic tone, respectively. The control unit is configured to control the intensity of respective stimulation pulses depending on a respective ANS indicating signal as generated by said ANS sensing unit.

18 Claims, 4 Drawing Sheets

APPARATUS AND METHOD FOR SPINAL CORD STIMULATION TO TREAT PAIN

CROSS-REFERENCE TO RELATED APPLICATIONS

This patent application claims the benefit of U.S. Provisional Patent Application No. 61/834,887, filed on Jun. 14, 2013, the disclosure of which is hereby incorporated by reference in its entirety.

TECHNICAL FIELD

The present invention concerns an apparatus and a method for spinal cord stimulation to treat pain.

BACKGROUND

Spinal cord stimulation ("SCS") based on implantable pulse generators has been used to treat chronic pain. The efficacy of spinal cord stimulation often decreases over time, likely due to a natural habituation response to the use of monotonically pulsed electrical fields and their regular induction of neural activity.

Recent art exists wherein electrical pulses from an implantable medical device are delivered with a time varying, including, for example, pseudo-random pulse frequency and/or pulse width. It has also been disclosed that stimulation can be applied in either tonic or burst patterns.

Arbitrary variation of the stimulation patterns, such as, for example, pseudo-random pulse frequency stimulation, burst stimulation, etc., has sub-optimal therapeutic effects.

In view of above, there is a need for an improved device and an improved method for spinal cord stimulation to treat pain.

The present invention is directed toward overcoming one or more of the above-identified problems.

SUMMARY

According to the present invention, at least one of the above needs is met by a spinal cord stimulation device having a stimulation unit for generation and delivery of stimulation pulses, a control unit for controlling the stimulation unit with respect to stimulation intensity, and an autonomic nervous system ("ANS") sensing unit that is configured to generate ANS indicating signals that represent an increased or elevated sympathetic tone or an increased or elevated parasympathetic tone, respectively. The control unit is configured to control the intensity of respective stimulation pulses depending on a respective ANS indicating signal as generated by the ANS sensing unit.

The present invention includes the recognition that there is a close relationship between pain perception and the autonomic nervous system ("ANS"), the status of which changes over time. The present inventive device allows dynamic adjustment of the spinal cord stimulation based on the status of ANS. The ANS sensing unit enables a feedback loop that incorporates physiological parameters in modulation of the spinal cord stimulation.

Thus, the present invention discloses an implantable spinal cord stimulation device which employs closed loop control to modulate the therapeutic intensity, by adjusting the stimulation parameters according to the status of the autonomic nervous system. The delivered stimulation pattern is also suited to reducing habituation and reducing stimulation power requirements.

According to a preferred embodiment, the control unit is configured to control the intensity of respective stimulation pulses such that relatively higher intensity stimulation pulses are generated in the case of ANS indicating signals representing an increased or elevated sympathetic tone, and relatively lower intensity stimulation pulses are generated in the case of ANS indicating signals representing increased or elevated parasympathetic tone. Thus, the stimulation device can adapt to a respective momentary status of the autonomic nervous system by adjusting the stimulation intensity in an adequate manner.

The ANS sensing unit is preferably configured to generate the ANS indicating signals from respiration signals that represent respiration activity. The ANS sensing unit preferably is further configured to determine from the respiration signals inspiration and the expiration phases and to generate respiration phase indicating signals accordingly. In such an embodiment, the control unit is preferably configured to control the intensity of respective stimulation pulses depending on respective respiration phase indicating signals received from the ANS sensing unit.

Thus, an effective therapy can be delivered by synchronizing the delivery of stimulation to the respiratory cycles and dynamically adjusting the stimulation parameters based on the sensory input from the respiration measurement.

Monitoring respiration activity by means of a respective sensor enables an implantable spinal cord stimulation device to treat pain in a closed loop control mode. This concept is developed based on the realization that: (a) there is a close relationship between pain perception and the status of the autonomic nervous system; and (b) there is a close relationship between respiration and the autonomic nervous system.

Accordingly, the control unit preferably is configured to control the intensity of respective stimulation pulses depending on a respective respiration phase indicating signal such that relatively higher intensity stimulation pulses are delivered at inspiration phases and relatively lower intensity stimulation pulses are delivered at expiration phases.

According to a further preferred embodiment, the ANS sensing unit comprises means to detect respiration signal and identify different phases of the respiration, for example, inspiration, expiration, post-inspiration pause, and post-expiration pause, and to generate a respiration indicating signal accordingly.

The control unit can be configured to dynamically adjust the stimulation intensity by means of varying stimulation frequency, pulse width or pulse amplitude or a combination thereof, in synchronization with received respiration phase indicating signals, such that high intensity stimulation pulses are delivered at increased sympathetic tones whereas lower intensity stimulation pulses are delivered at increased parasympathetic tones.

In its preferred embodiment, the device has a means to detect respiration signals and identify different phases of the respiration, for example, inspiration, expiration, post-inspiration pause, and post-expiration pause. The device then dynamically adjusts the stimulation intensity, e.g., by means of varying stimulation frequency, pulse width, pulse amplitude, etc., in synchronization with the detected respiration phases, such that high intensity spinal cord stimulation is delivered at increased sympathetic tones whereas lower intensity spinal cord stimulation is delivered at increased parasympathetic tones. By synchronizing the stimulation intensity with respiration phases, the device achieves closes loop control that can improve the efficacy and efficiency of the spinal cord stimulation therapy. In addition, by adapting spinal cord stimulation with the physiological breathing, the varying stimulation intensity can minimize the habituation response. The periodic pause or reduced stimulation intensity can also reduce power consumption.

To enable efficient determination of respiration phases, the device preferably comprises a respiration sensing unit that is connected to the ANS sensing unit and that is configured to sense values of an electric parameter which are depending on a respective respiration phase. In a preferred embodiment, the respiration sensing unit comprises an impedance sensing unit that is configured to sense a transthoracic impedance and generate transthoracic impedance signals that represent values of sensed transthoracic impedance.

The transthoracic impedance signals allow determination of the respiration signals and, thus, of the respiration phase indicating signals that are one kind of ANS indicating signals.

In such embodiment, the ANS sensing unit in combination with the respiration sensing unit can be configured to continuously analyze acquired transthoracic impedance signals to detect different phases of the respiratory cycle and to determine respiration parameters such as, for example, the respiration rate, tidal volume and/or minute ventilation.

The control unit can be configured to modulate the stimulation pulses' intensity by running a closed loop control algorithm using at least one of respiration rate, tidal volume and minute ventilation.

According to a further aspect of the present invention, this need mentioned above is met by a method for controlling a spinal cord stimulation device. The method comprises the steps of:
- acquiring values of a parameter that is indicative for a status of an autonomic nervous system,
- evaluating acquired values of said parameter that is indicative for a status of an autonomic nervous system and generating a control signal based on the evaluation, and
- controlling generation of stimulation pulses depending on said control signal.

The parameter that is indicative for a status of an autonomic nervous system preferably is respiration activity. Of course, other parameters are contemplated herein. The evaluation of acquired values that represent respiration activity preferably includes a determination respiration phases such as, for example, inspiration and expiration.

Preferably, the control signal is generated in dependence of a determined respiration phase so that the control signal causes generation of stimulation pulses with a relatively higher intensity in inspiration phases and generation of stimulation pulses with a relatively lower intensity is caused in expiration phases.

A further aspect refers to the treatment of pain with a method disclosed herein. The method comprises delivery of stimulation pulses that are generated in a controlled manner as pointed out above.

Further features, aspects, objects, advantages, and possible applications of the present invention will become apparent from a study of the exemplary embodiments and examples described below, in combination with the Figures, and the appended claims.

DESCRIPTION OF THE DRAWINGS

The above and other aspects, features and advantages of the present invention will be more apparent from the following more particular description thereof, presented in conjunction with the following drawings wherein.

DETAILED DESCRIPTION

The following description is of the best mode presently contemplated for carrying out the present invention. This description is not to be taken in a limiting sense, but is made merely for the purpose of describing the general principles of the present invention. The scope of the present invention should be determined with reference to the claims.

Figure 1:
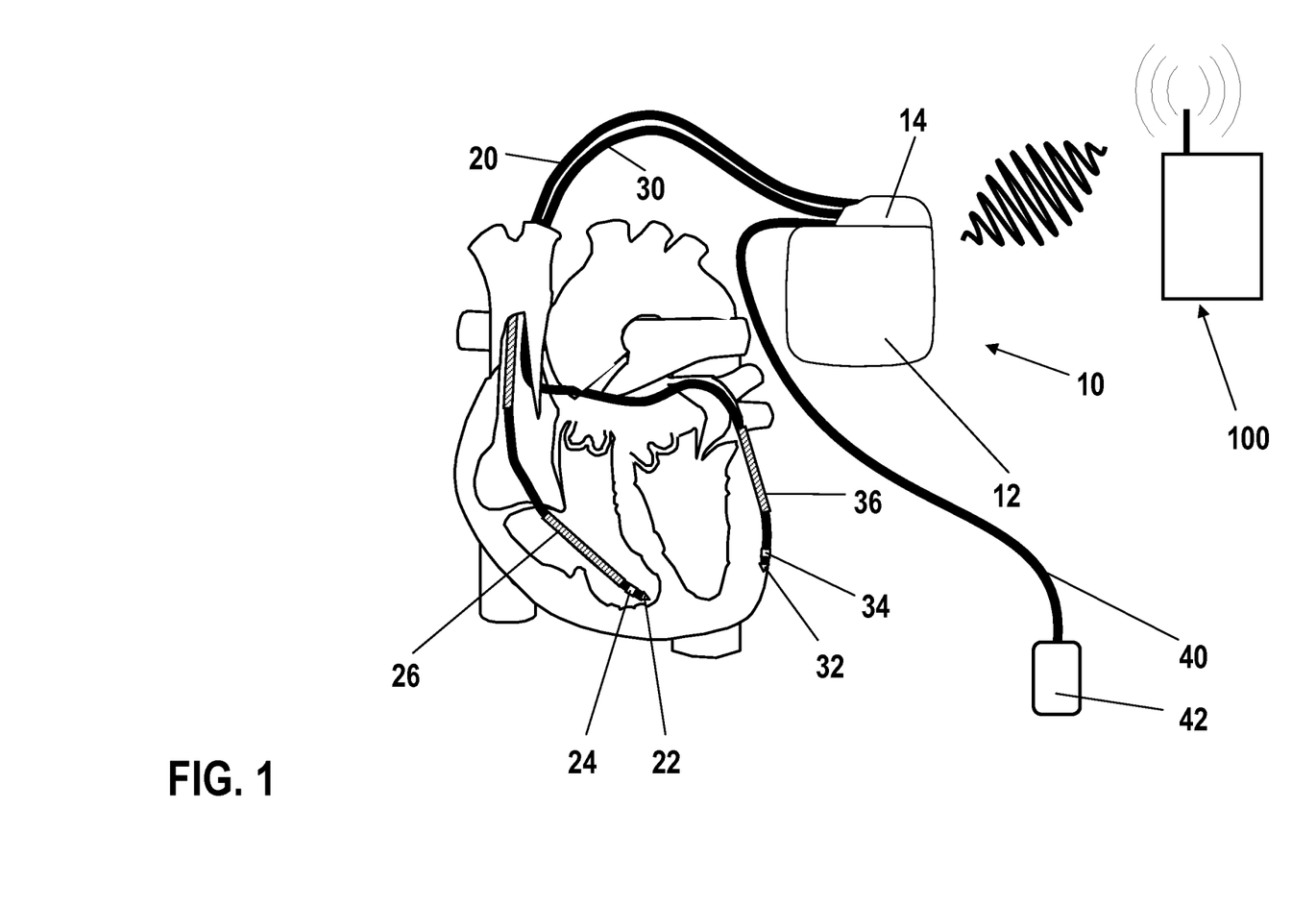
FIG. 1 shows an implantable medical device including a spinal cord stimulation ("SCS") device connected to leads which in part are placed in a heart.
Figure 2:
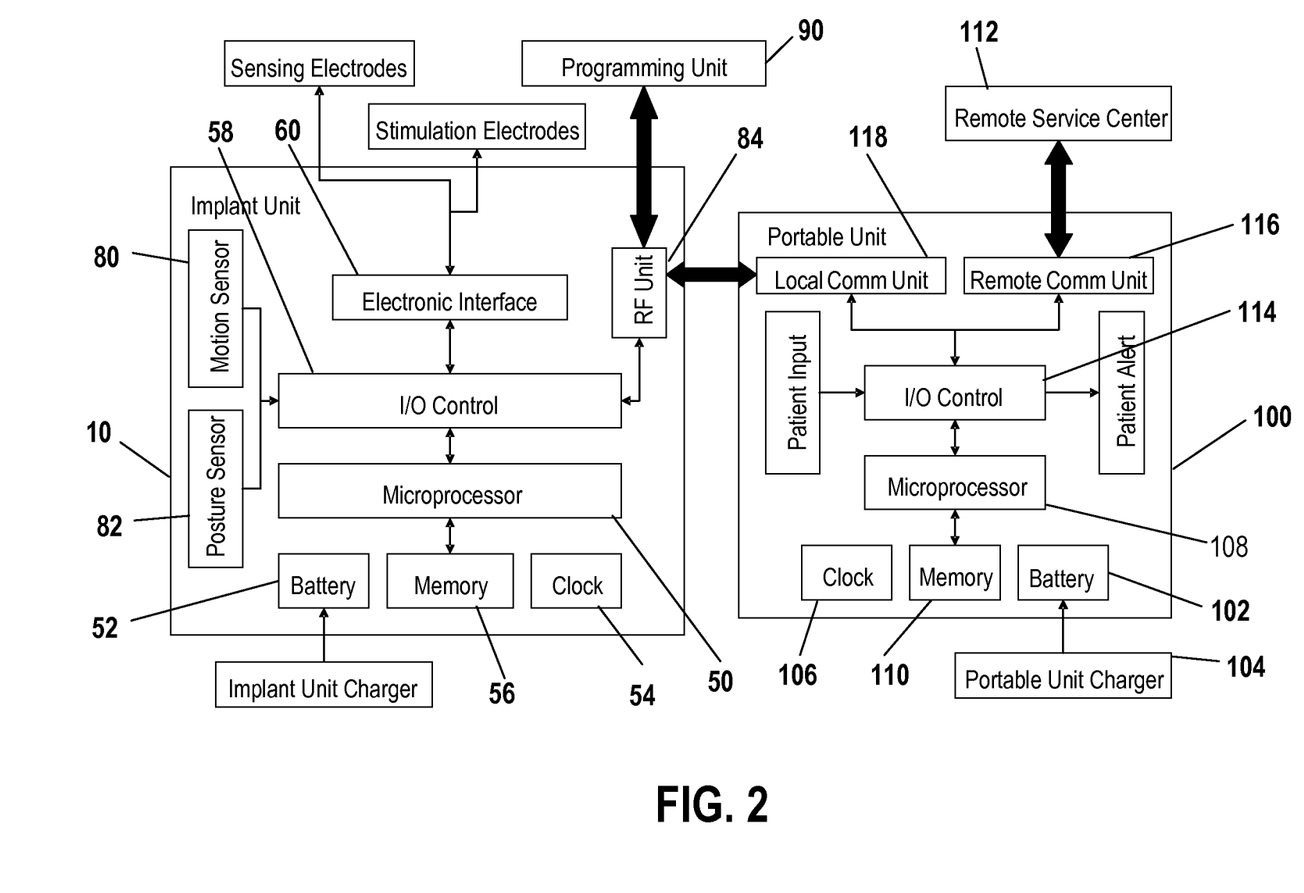
FIG. 2 is a schematic block diagram illustrating some internal components of the spinal cord stimulation device depicted in FIG. 1.
Figure 3:
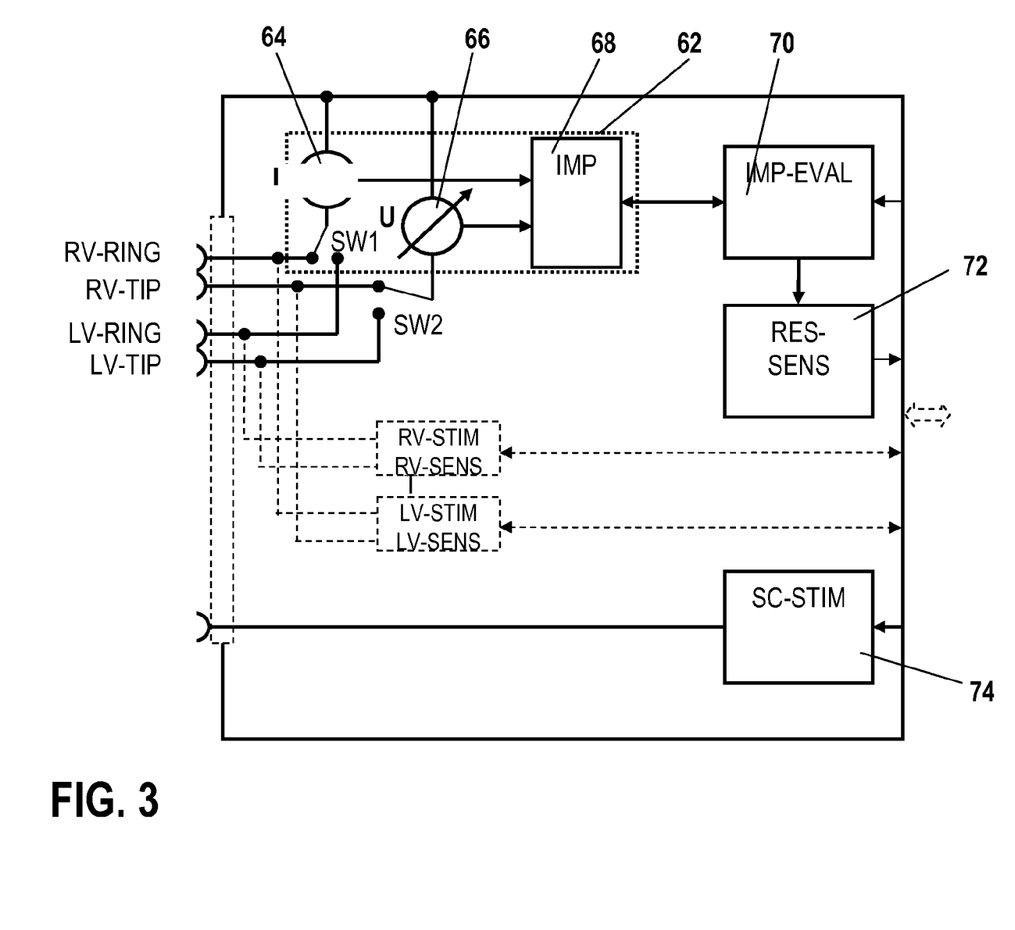
FIG. 3 is a schematic block diagram of the electronic interface of the device illustrated in FIG. 2.

FIGS. 1-3 schematically illustrate a spinal cord stimulation system disclosed in accordance with the present invention, comprising an implant unit 10, which interfaces with an external programming unit 100, an external portable device, which further communicates with the remote service center 112.

In the example illustrated in FIGS. 1-3, the spinal cord stimulation device is integrated into an implantable cardiac stimulation device that is configured to determine a transthoracic impedance. It is noted that the spinal cord stimulation device can be realized independently from a cardiac stimulator.

The implant unit 10 comprises an electronic circuitry that is hermetically sealed inside a can 12 (i.e., a housing), which is made from a biocompatible conductive material such as, for example, titanium. A non-conductive header 14 is attached to the can 12. A plurality of electrodes 22, 24, 26, 32, 34, 36 and 42, which are electrically isolated from one another, are connected to the header 14 via one or more subcutaneous leads 20, 30 and 40.

Enclosed inside the hermetically sealed can 12, a microprocessor 50 and associated circuitry make up the controller of the implant unit 10. The implant unit 10 is powered by a battery 52, and maintains an internal clock 54 for timing the operations. The microprocessor 50 communicates with a memory 56 via a bi-directional data bus. The memory 56 typically comprises a ROM or RAM for program storage and a RAM for data storage. The microprocessor 50 connects to an I/O control unit 58, which further connects to an electronic interface 60, to manage the input and output of the implant unit 10. By running the program stored in the memory 56, the microprocessor 50 controls how input signals are acquired (e.g., gain, offset, filter settings, sampling frequency, sampling resolution, etc.) and how stimulation pulses are delivered (e.g., frequency, amplitude, pulse width, etc.).

The electrodes are connected to the electronic interface 60 that preferably includes a feed-through circuitry for noise reduction, a high voltage protection circuitry, a switch network circuitry for sensing and stimulating channel selection, and front-end analog filters, as are well known in the field. The configurations of the interface circuitry (e.g., filter settings, sensing channel selection, etc.) can be programmed by the microprocessor 50.

Details of the interface unit 60 are illustrated in FIG. 3. For impedance measurement, an impedance measurement unit 62 is provided. Impedance measurement unit 62 comprises a constant current source 64 that is connected or can be connected to electrodes for intracorporeal placement, as shown in FIG. 1. In order to allow for a plurality of impedance measurement electrode configurations, preferably some means of switching is provided between the constant current source 64 and the electrode terminals of the implantable medical device 10. In FIG. 3 switches SW1 and SW2 are shown.

As an alternative to constant current source 64, a constant voltage source can be provided. Then, the measuring unit will be adapted to measure a current strength of a current fed through a body by the constant voltage source.

Both the constant current source 64 and the measuring unit 66 are connected to an impedance value determination unit 68 that is adapted to determine an impedance value for each measuring current pulse delivered by the constant current source 64.

Further, an impedance evaluation unit 70 is provided, that is connected to the impedance determination unit 68 and that is adapted to control the impedance determination unit 68 and to evaluate a sequence of consecutive impedance values determined by the impedance measurement unit 62. Impedance measurement unit 62 and impedance evaluation unit 70 together serve as an impedance sensing unit for acquiring impedance values that can be further processed by a respiration sensing unit 72. Impedance evaluation unit 70 is also connected to the respiration sensing unit 72.

The impedance measurement unit 62 is adapted to determine at least transthoracic impedance values and, in addition, preferably intracardiac impedance values for the same period of time, wherein the transthoracic impedance values are sampled with a lower sampling rate than the intracardiac impedance values.

One or more electrodes 42 connected to the implant unit 10 via lead 40 are stimulation electrodes that are used for the delivery of electrical pulses to the target spinal cord area(s) for pain treatment. As known in the art, these electrodes 42 can be designed to have different forms, such as, for example, ring electrodes, cuff electrodes, patch electrodes, etc. Other sensing electrodes are also connected to the electronic controller. These sensing electrodes 22, 24, 32, 34 can detect electrical signals, such as, for example, the subcutaneous or intracardiac ECG signals, from the body tissue.

Stimulation electrode 42 is connected to a spinal cord stimulation unit 74 that is controlled by the microprocessor 50. Further stimulation and/or sensing units may be provided to allow for instance cardiac stimulation or sensing of intracardiac ECG signals, as indicated in FIGS. 2 and 3.

The sensing electrodes can detect an impedance signal (Z). By injecting a small constant current (e.g., 100 µA, preferably biphasic) between two electrodes while measuring the voltage difference between the same or different pair of electrodes, the impedance is calculated as the ratio between the measured voltage difference and the injecting current strength. As known in the art, the impedance signal provides useful information on the integrity of the sensing or stimulating channel. In addition, the measured impedance signal, particularly the transthoracic impedance signal, may be further processed by the microprocessor 50 to extract the respiration information.

Other types of biological signals measured by specific sensors can also serve as an input to the implant device 10. For example, an on-board accelerometer can serve as a motion sensor 80 that provides patient's activity signal to the implant device 10, and an on-board posture sensor 82 can provide patient's posture change information to the implant device 10. Other types of input signals include, but are not limited to, the subcutaneous pressure signal measured by a pressure sensor, the subcutaneous temperature signal measured by a temperature sensor, the subcutaneous pH signal measured by a pH sensor, etc.

The acquired physiological signals are stored in the device memory 56 and analyzed by the microprocessor 50 by running programmed algorithms. For example, the microprocessor 50 continuously analyzes the acquired transthoracic impedance signals to detect different phases of the respiratory cycle and measure the respiration parameters such as, for example, the respiration rate, tidal volume, minute ventilation, etc. Based on these measurements, the microprocessor can then modulate the stimulation pulses by running a closed loop control algorithm.

The implant unit 10 also includes a radio-frequency ("RF") telemetry unit 84. The RF telemetry unit 84 may be of the type well known in the art for sending information which it obtains from the implant device 10 to the external programmer 90, or for receiving programming parameters from the external programmer 90 and then conveying the same to the implant device 10. In one typical embodiment, the external programmer 90 can interrogate the implant device 10 to get the status of the implant device 10 (e.g., battery status, channel impedance, etc.) or the data recorded by the implant device 10. In another typical embodiment, the external programmer 90 can be used to activate or deactivate selected algorithms or update programmable parameters of the implant device 10.

In addition, the external portable unit 100, to be described hereinafter, can also communicate bi-directionally with the implant unit 10 through the telemetry unit 84. Preferably, the data that may be received from or sent to the external portable unit 100 are more limited as compared to the data that may be received from or sent to the external programmer 90.

In a preferred embodiment, the data that are transmitted from the external portable unit 100 to the implant device 10 are simple commands, such as, for example, change the spinal cord stimulation protocol, adjusting the stimulation parameters, retrieve most recently diagnostic information from the implanted unit, etc. These commands set the implant unit 10 into one of a number of modalities, wherein each modality is determined and controlled by parameters that can only be selected by a physician operating the external programmer 90 using secure passwords or codes.

The data that are transmitted from the implant unit 10 to the external portable unit 100 preferably include simple acknowledgments to confirm receiving the commands from the external portable unit 100, the signals warning the detection of abnormal conditions, such as, for example, detection of abnormal lead impedance, detection of abnormal temperature, and so on. Other diagnostic information, such as, for example, the measured respiration parameters, snapshots of recorded physiological signals, etc., can also be transmitted to the external portable unit 100. Preferably, a physician operating the external programmer 90 using secure password or codes controls the enable/disable condition as well as the amount of data that can be transmitted from the implant unit 10 to the external portable unit 100.

Still referring to FIG. 2, the external portable unit 100 has a power source, such as, for example, a lithium battery 102, which provides power to the electrical components of the device 100. The battery 102 is chargeable by connecting to an external charger 104. The external portable device 100 also maintains an internal clock 106 for timing its operations. The overall functioning of the external portable unit 100 is controlled by its microprocessor 108, which reads and performs instructions stored in its associated memory 110. The instructions stored in memory 110 preferably include instructions defining a communication protocol compatible with the implant unit 10, and instructions defining a communication protocol compatible with the remote service center 112.

The microprocessor 108 of the external portable unit 100 communicates with an I/O control unit 114 to read from the keypad or press switches the patient input commands. For example, one subset of the input commands is designed to configure the external portable unit 100, e.g., to select specific communication protocols. Another subset of the input commands is designed to establish communication between the external portable unit 100 and the remote service center 112 via remote communication unit 116. For example, a patient's input can command the external portable unit 100 to transmit information retrieved from the implant unit 10 to the remote service center 112, and wait to receive acknowledgement. The third subset of the commands is designed to establish communication between the external portable unit 100 and the implant unit 10 via implant communication unit 116. For example, a patient's input can command the external portable unit 100 to transmit corresponding signals to the implant unit 10 to change stimulation protocol, to adjust the stimulation parameters, to retrieve information from the implanted unit 10, etc. The implant communication unit 116 also receives the acknowledgement and related device information sent from the implant unit 10, and conveys these data to the microprocessor 108 for storage in the memory 110.

According to one exemplary embodiment of the present invention, upon receiving a predefined warning signal from the implant device 10 (e.g., detection of low battery, detection of abnormal lead impedance, etc.), the microprocessor 108 of the external portable unit 100 communicates with the I/O control unit 114 to generate output that is perceptible by the patient. Such output can be in the form of visible message, such as, for example, the light-up or blinking of a light emitting diode ("LED"), or the text message displayed in a liquid crystal display ("LCD"), or in the form of audible message such as beep, ringing tone, or pre-recorded voice messages played by a speaker, or in the form of discernible vibration by a vibrator. Besides generating warning messages, some diagnostic information that is received from the implant unit 10 can also be provided to the patient in the form of visual or audible messages.

The external portable unit 100, via its remote communication unit 116, can further communicate with the remote service center 112. Such long-range communication apparatus can be in the form of a mobile radio network, or a landline telecommunication network, or the internet, as well known in the art. Examples of such long-range communication apparatus have been taught in U.S. Pat. Nos. 6,470,215, 6,574,509, and 6,622,043, all of which are assigned to the Assignee of the present invention and incorporated herein by reference in their entireties.

In one typical embodiment, the external portable unit 100 transmits the implant unit status information (e.g., battery status, lead impedance, etc.) as well as relevant diagnostic information (e.g., respiration rate, etc.) to the remote service center 112 according to a predefined transmission frequency and schedule. Yet in another typical embodiment, the external portable unit 100 communicates with the remote service center 112 in a trigger mode, for example, upon receiving a warning signal from the implant unit 10, or upon the patient trigger. In such cases, the external portable unit 100 transmits critical diagnostic information stored in device memory 110 to the remote service center 112.

The remote service center 112 receives the information via compatible communication protocols, and then sends acknowledgement back to the external portable unit 100, which may generate visible or audible output indicating receipt of the acknowledgement. The data received by the remote service center 112 is stored in a central database, and is promptly presented to the patient's physician or responsible personnel through proper means, such as, for example, fax, email, text message, etc., as known in the art. By reviewing the received diagnostic information, the physician can evaluate the patient's condition and provide expert advice to the patient who wishes to contact the physician before taking any action in response to the warning signals generated by the external portable device 100.

According to the present invention, the spinal cord stimulation system controls the delivery of stimulation pulses to the spinal cord for the treatment of pain by means of synchronization with the respiration. The concept of the present invention is developed based on the realization that: (a) there is a close relationship between pain perception and the status of the autonomic nervous system; and (b) there is a close relationship between respiration and the autonomic nervous system.

Although the role of the autonomic nervous system in chronic pain is not fully understood, there is good evidence that the sympathetic nervous system plays a major role in sustaining chronic pain. The sympathetic nervous system is the part of the autonomic nervous system which prepares the body for stressful or emergency situations and promotes the flight or fight response. Pain receptors are part of the sympathetic nervous system. Moreover, an overloaded sympathetic nervous system can heighten anxiety which in turn amplifies pain perception. It has been found that damaged afferent fibers may develop a sensitivity to sympathetic stimulation, both at the site of injury and more centrally, particularly the dorsal horns. It has also been shown that every part of the peripheral nervous system, from dorsal root ganglion all the way to the pain receptors in the periphery, has a post-ganglionic sympathetic supply which increases both sensory receptor sensitivity and nerve conduction speeds. On the other hand, the parasympathetic system is the branch of the autonomic nervous system responsible for the body's ability to recuperate and return to a balanced state, or homeostasis, after experiencing pain or stress. The vagus nerve is the principal nerve involved in effecting parasympathetic activity to most areas of the body.

Although the spinal cord stimulation has been an established therapy for the treatment of pain, the neurophysiologic mechanisms of spinal cord stimulation are not completely understood. However, some research suggests that its effects occur at local and supra-spinal levels, and also through dorsal horn interneuron and neurochemical mechanisms. It has been hypothesized that the action of spinal cord stimulation may differ depending on the type of pain targeted for treatment. For example, its effect on neuropathic pain may be secondary to stimulation-induced suppression of central excitability, whereas the beneficial effect of spinal cord stimulation on ischemic pain may be related to stimulation-induced inhibition of sympathetic nervous system influences and antidromic vasodilation, which increases blood flow and reduces oxygen demand. Regardless of the specific mechanism, spinal cord stimulation seems to mask or alter the patient's sensation of pain through a modulating effect on the patient's autonomic nervous system. In particular, it is reasonable to hypothesize that the spinal cord stimulation may affect the autonomic nervous system by promoting parasympathetic system activity and down-regulating the sympathetic nervous system.

It has been well known that spontaneous respiration is modulated by the autonomic nervous system. Increased sympathetic activity results in an increase in respiration rate, whereas increased parasympathetic results in a lower respiration rate. On the other hand, controlled breathing can also modulate the autonomic nervous system. For example, deep and slow breathing can shift the autonomic tone toward parasympathetic predominance, whereas fast and shallow breathing can shift the autonomic tone toward sympathetic predominance.

Moreover, spontaneous respiration can also affect the heart rate, known as respiratory sinus arrhythmia ("RSA"), through modulation of the autonomic nervous system. RSA is a rhythmical fluctuation in heart rate at the respiratory frequency that is characterized by an increase and decrease of heart rate in a phase relationship with inspiration and expiration, respectively. The increase in heart rate is indicative of a net increase in sympathetic emphasis during inhalation, and the decrease in heart rate is indicative of a net increase in parasympathetic emphasis during exhalation. When inhaling and exhaling with depth and regularity, autonomic status swings from parasympathetic to sympathetic (inhalation) and from sympathetic to parasympathetic (exhalation). The physiological origins of RSA are thought to relate to the central respiratory generator, which modulates autonomic outflow through relatively direct central synaptic actions. Vagal cardiomotor neurons are inhibited during inspiration and are mildly activated during expiration. In contrast, sympathetic motor neurons are excited during inspiration and are mildly inhibited during expiration. Such phasic (excitatory/inhibitory) modulation of automonic motor neurons by the respiratory generator would contribute to respiratory-frequency modulations in both sympathetic and vagal outflows. Therefore, RSA is frequently employed as an index of cardiac vagal tone or even believed to be a direct measure of the vagal tone.

Figure 4:
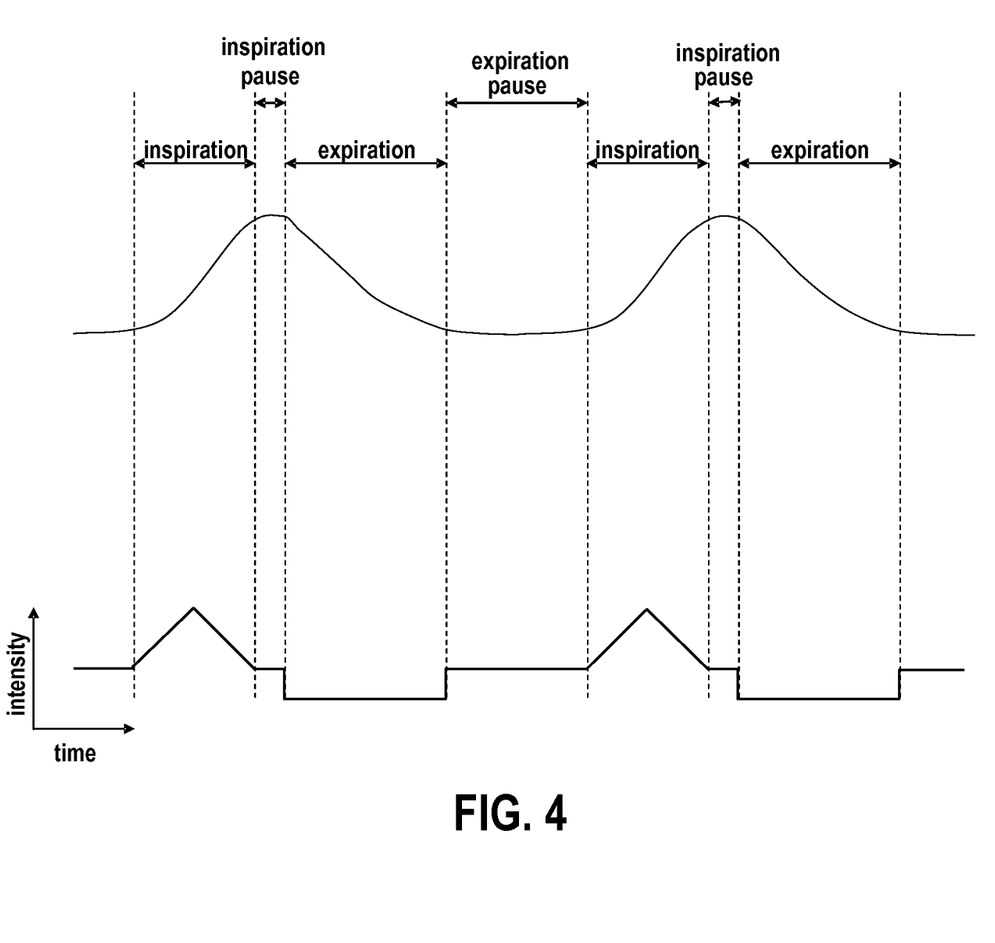
FIG. 4 is a schematic illustration of the respiration synchronized stimulation.

The method for respiration synchronized spinal cord stimulation is illustrated in FIG. 4 and disclosed hereinafter.

According to the present invention, the device has a means to detect respiration signals. The respiration signal can be extracted from many types of physiological signals that are modulated by respiration, such as, for example, the transthoracic impedance signal, the surface or subcutaneous ECG signal, the pulse pressure signal, the oxygen saturation signal, and so on. As known in the art, different techniques, such as, for example, linear or nonlinear filters, supervised or unsupervised blind source separation methods, etc., can be applied to extract the respiration signal from the above mentioned physiological signals. By identifying the peaks and nadirs of the extracted respiration signal, different phases of the respiration cycle can be determined, such as, for example, inspiration, expiration, post-inspiration pause, and post-expiration pause, as illustrated in FIG. 4.

According to the present invention, the device then dynamically adjusts the stimulation intensity, e.g., by means of varying stimulation frequency, pulse width, pulse amplitude, pulse shape, etc., in synchronization with the detected respiration phases. In one exemplary embodiment, the pulse amplitude is increased or decreased to increase or decrease the stimulation intensity, respectively. In another embodiment, the stimulation frequency is adjusted upward or downward to increase or decrease the stimulation intensity, respectively.

According to the present invention, higher intensity spinal cord stimulation is delivered during the inspiration phase when the sympathetic tone is elevated, whereas lower intensity or no spinal cord stimulation is delivered during the expiration phase when the parasympathetic tone is elevated. During the phases of inspiration pause or expiration pause, intermediate intensity spinal cord stimulation or optionally no spinal cord stimulation is delivered.

According to one typical embodiment of the present invention, the intensity of spinal cord stimulation (shown at the top of the graph in FIG. 4) is further adapted to the first derivative (or slope) of the respiration signal (shown at the bottom of the graph in FIG. 4), in addition to the respiration phases, as illustrated in FIG. 4. Denote: "Iins" the intensity of spinal cord stimulation during the inspiration phase; "Iexp" the intensity of spinal cord stimulation during the expiration phase; "Iip" the intensity of spinal cord stimulation during the inspiration pause; and "Iep" the intensity of spinal cord stimulation during the expiration pause. In a typical embodiment, Iins is dynamically adjusted during the inspiration phase, whereas Iexp, Iip and Iep have predefined or user-programmable constant values. During the inspiration phase, the slope of the respiration signal first increases (starting from the nadir of the respiration signal), then decreases (until reaching the peak of the respiration signal). In a parallel pattern, the spinal cord stimulation intensity Iins first increases then decreases during the inspiration phase. The respective spinal cord stimulation intensity during inspiration and expiration pauses, Iip and Iep, can be set to the same value or different values, but preferably both of them are lower than, or equal to, the minimum of Iins. The spinal cord stimulation intensity during the expiration phase, Iexp, is preferably lower than, or equal to, Iip and/or Iep. In one embodiment, Iexp is set to zero, i.e., spinal cord stimulation is turned off during the expiration phase.

Therefore, as illustrated in FIG. 4, while the spinal cord stimulation intensity ramps up or down during the inspiration phase, in general it maintains a higher level of stimulation intensity to counter the elevated sympathetic tone for enhanced pain treatment. On the other hand, reduced spinal cord stimulation intensity is applied during the expiration phase (and/or respiration pauses) when the parasympathetic tone is elevated and thus less intensive pain treatment may be needed.

The respiration-synchronized stimulation protocol is further adaptive to the general autonomic status of the patient. For example, when patient's sympathetic tone is elevated during stress conditions, the breathing pattern generally becomes fast and shallow. As a result, the patient spends higher proportion of time period in the inspiration phase. Consequently, higher doses of spinal cord stimulation are delivered for enhanced pain treatment. On the other hand, when the patient's parasympathetic tone is elevated during relaxed conditions, the breathing pattern generally becomes slow and deep. As a result, the patients spent higher proportion of time period in the expiration phase. Consequently, fewer doses of spinal cord stimulation are delivered.

The present invention has a number of unique advantages.

First, by synchronizing the stimulation intensity with respiration phases, or more specifically, by increasing the intensity of spinal cord stimulation during inspiration and reducing the intensity of spinal cord stimulation during expiration, the device can improve the efficacy and efficiency of the spinal cord stimulation therapy.

Second, by adapting spinal cord stimulation with the physiological breathing, the varying stimulation intensity can minimize the habituation response.

Third, the periodic pause or reduced stimulation intensity can also reduce power consumption.

Finally, the present invention represents a novel approach for closed loop control of spinal cord stimulation, which may affect the autonomic nervous system by promoting parasympathetic system activity and down regulating the sympathetic nervous system, thus achieving more effective pain treatment.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A spinal cord stimulation device comprising:
   a stimulation unit for generation and delivery of stimulation pulses;
   a control unit for controlling the stimulation unit with respect to stimulation intensity; and
   an autonomic nervous system ("ANS") sensing unit that is configured to generate ANS indicating signals representing an increased sympathetic tone or an increased parasympathetic tone, respectively, said control unit being configured to control the intensity of respective stimulation pulses depending on a respective ANS indicating signal as generated by said ANS sensing unit,
   wherein the ANS sensing unit is configured to generate said ANS indicating signals from respiration signals that represent respiration activity, and wherein the ANS sensing unit is further configured to determine from the respiration signals inspiration and expiration phases and to generate respiration phase indicating signals accordingly,
   wherein the control unit is configured to dynamically adjust the stimulation intensity by means of varying stimulation frequency, pulse width or pulse amplitude, or a combination thereof, in synchronization with received respiration phase indicating signals, such that high intensity stimulation pulses are delivered at increased sympathetic tone whereas lower intensity stimulation pulses are delivered at increased parasympathetic tone.

2. The spinal cord stimulation device according to claim 1, wherein the control unit is configured to control the intensity of respective stimulation pulses such that relatively higher intensity stimulation pulses are generated in case of ANS indicating signals representing an increased sympathetic tone and relatively lower intensity stimulation pulses are generated in case of ANS indicating signals representing an increased parasympathetic tone.

3. The spinal cord stimulation device according to claim 2, wherein said control unit is configured to control the intensity of respective stimulation pulses depending on respective respiration phase indicating signals received from said ANS sensing unit.

4. The spinal cord stimulation device according to claim 3, wherein the ANS sensing unit comprises means to detect respiration signals and identify different phases of the respiration and to generate a respiration indicating signal accordingly, wherein the different phases of the respiration include inspiration, expiration, post-inspiration pause, and post-expiration pause.

5. The spinal cord stimulation device according to claim 1, wherein the control unit is configured to control the intensity of respective stimulation pulses depending on a respective respiration phase indicating signal such that relatively higher intensity stimulation pulses are delivered at inspiration phases and relatively lower intensity stimulation pulses are delivered at expiration phases.

6. The spinal cord stimulation device according to claim 1, further comprising a respiration sensing unit that is connected to said ANS sensing unit and is configured to sense values of an electric parameter which are depending on a respective respiration phase.

7. The spinal cord stimulation device according to claim 6, wherein said respiration sensing unit comprises an impedance sensing unit that is configured to sense a transthoracic impedance and generate transthoracic impedance signals that represent values of sensed transthoracic impedance.

8. The spinal cord stimulation device according to claim 6, wherein said ANS sensing unit in combination with said respiration sensing unit is configured to continuously analyze acquired transthoracic impedance signals to detect different phases of the respiratory cycle and to determine respiration parameters including respiration rate, tidal volume and/or minute ventilation.

9. The spinal cord stimulation device according to claim 6, wherein said control unit is configured to modulate the stimulation pulses' intensity by running a closed loop control algorithm using at least one of respiration rate, tidal volume and minute ventilation.

10. A spinal cord stimulation device comprising:
    a stimulation unit for generation and delivery of stimulation pulses;
    a control unit for controlling the stimulation unit with respect to stimulation intensity; and
    an autonomic nervous system ("ANS") sensing unit that is configured to generate ANS indicating signals representing an increased sympathetic tone or an increased parasympathetic tone, respectively, said control unit being configured to control the intensity of respective stimulation pulses depending on a respective ANS indicating signal as generated by said ANS sensing unit,
    wherein the ANS sensing unit is configured to generate said ANS indicating signals from respiration signals that represent respiration activity, and wherein the ANS sensing unit is further configured to determine from the respiration signals inspiration and expiration phases and to generate respiration phase indicating signals accordingly, said control unit being configured to control the intensity of respective stimulation pulses in synchronization with respective respiration phase indicating signals received from said ANS sensing unit,
    wherein the control unit is configured to dynamically adjust the stimulation intensity by means of varying stimulation frequency, pulse width or pulse amplitude, or a combination thereof, in synchronization with received respiration phase indicating signals, such that high intensity stimulation pulses are delivered at increased sympathetic tone whereas lower intensity stimulation pulses are delivered at increased parasympathetic tone.

11. The spinal cord stimulation device according to claim 10, wherein the ANS sensing unit comprises means to detect respiration signals and identify different phases of the respiration and to generate a respiration indicating signal accordingly, wherein the different phases of the respiration include inspiration, expiration, post-inspiration pause, and post-expiration pause.

12. The spinal cord stimulation device according to claim 10, further comprising a respiration sensing unit that is connected to said ANS sensing unit and is configured to sense values of an electric parameter which are depending on a respective respiration phase.

13. The spinal cord stimulation device according to claim 12, wherein said respiration sensing unit comprises an impedance sensing unit that is configured to sense a transthoracic impedance and generate transthoracic impedance signals that represent values of sensed transthoracic impedance.

14. The spinal cord stimulation device according to claim 12, wherein said ANS sensing unit in combination with said respiration sensing unit is configured to continuously analyze acquired transthoracic impedance signals to detect different phases of the respiratory cycle and to determine respiration parameters including respiration rate, tidal volume and/or minute ventilation.

15. The spinal cord stimulation device according to claim 12, wherein said control unit is configured to modulate the stimulation pulses' intensity by running a closed loop control algorithm using at least one of respiration rate, tidal volume and minute ventilation.

16. A spinal cord stimulation device comprising:
a stimulation unit for generation and delivery of stimulation pulses;
a control unit for controlling the stimulation unit with respect to stimulation amplitude; and
an autonomic nervous system ("ANS") sensing unit that is configured to generate ANS indicating signals representing an increased sympathetic tone or an increased parasympathetic tone, respectively, said control unit being configured to control the amplitude of respective stimulation pulses depending on a respective ANS indicating signal as generated by said ANS sensing unit,
wherein the control unit is configured to control the amplitude of respective stimulation pulses such that relatively higher amplitude stimulation pulses are generated in case of ANS indicating signals representing an increased sympathetic tone and relatively lower amplitude stimulation pulses are generated in case of ANS indicating signals representing an increased parasympathetic tone.

17. The spinal cord stimulation device recited in claim 16, wherein the ANS sensing unit is configured to generate said ANS indicating signals from respiration signals that represent respiration activity, and wherein the ANS sensing unit is further configured to determine from the respiration signals inspiration and expiration phases and to generate respiration phase indicating signals accordingly, said control unit being configured to control the amplitude of respective stimulation pulses depending on respective respiration phase indicating signals received from said ANS sensing unit.

18. A spinal cord stimulation device comprising:
a stimulation unit for generation and delivery of stimulation pulses;
a control unit for controlling the stimulation unit with respect to stimulation amplitude; and
an autonomic nervous system ("ANS") sensing unit that is configured to generate ANS indicating signals representing an increased sympathetic tone or an increased parasympathetic tone, respectively, said control unit being configured to control the amplitude of respective stimulation pulses depending on a respective ANS indicating signal as generated by said ANS sensing unit,
wherein the control unit is configured to control the amplitude of respective stimulation pulses depending on a respective respiration phase indicating signal such that relatively higher amplitude stimulation pulses are delivered at inspiration phases and relatively lower amplitude stimulation pulses are delivered at expiration phases.

* * * * *